US012427014B2

(12) United States Patent
Perkins et al.

(10) Patent No.: US 12,427,014 B2
(45) Date of Patent: Sep. 30, 2025

(54) AORTIC LANDING BAND SUPPORT METHOD AND SYSTEM

(71) Applicant: Medtronic Vascular, Inc., Santa Rosa, CA (US)

(72) Inventors: Keith Perkins, Santa Rosa, CA (US); Mark Stiger, Santa Rosa, CA (US); Steven Claessens, Santa Rosa, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 0 days.

(21) Appl. No.: 18/114,745

(22) Filed: Feb. 27, 2023

(65) Prior Publication Data

US 2023/0218385 A1 Jul. 13, 2023

Related U.S. Application Data

(63) Continuation of application No. 17/354,629, filed on Jun. 22, 2021, now Pat. No. 11,617,641.

(51) Int. Cl.
*A61F 2/24* (2006.01)
*A61F 2/07* (2013.01)
*A61F 2/848* (2013.01)

(52) U.S. Cl.
CPC .............. *A61F 2/2409* (2013.01); *A61F 2/07* (2013.01); *A61F 2/24* (2013.01); *A61F 2/848* (2013.01);
(Continued)

(58) Field of Classification Search
CPC ..... A61F 2/2478–2482; A61F 2/07–2002/077; A61F 2/24–2002/2424;
(Continued)

(56) References Cited

U.S. PATENT DOCUMENTS 5,582,616 A * 12/1996 Bolduc ................ A61B 17/064
606/139
6,669,707 B1 * 12/2003 Swanstrom ............... A61F 2/07
606/151
(Continued)

FOREIGN PATENT DOCUMENTS

WO 9739687 A1 10/1997
WO 9806355 A1 2/1998
(Continued)

OTHER PUBLICATIONS

Extended European Search Report in European Application No. 22178595.9, mailed Nov. 17, 2022, 8 pages.

*Primary Examiner* — Rebecca S Preston
(74) *Attorney, Agent, or Firm* — Brooks Kushman P.C.

(57) ABSTRACT

A method of providing support in an aortic region. The method includes wrapping a landing band around an outside of a portion of an aortic vessel in a vicinity of a sinotubular junction (STJ) to form a wrapped portion of the aortic vessel. The method further includes securing the landing band to form a secured landing band. The method also includes endovascularly delivering a stent graft in a radially constricted configuration into the aortic vessel. The method also includes deploying the stent graft to a radially expanded configuration such that the stent graft contacts the wrapped portion of the aortic vessel. The method also includes connecting the stent graft in the radially expanded configuration to the secured landing band.

20 Claims, 13 Drawing Sheets

(52) U.S. Cl.
CPC .............. *A61F 2220/0016* (2013.01); *A61F 2220/0075* (2013.01); *A61F 2230/0067* (2013.01); *A61F 2250/001* (2013.01); *A61F 2250/0039* (2013.01); *A61F 2250/0069* (2013.01); *A61F 2250/0097* (2013.01)

(58) Field of Classification Search
CPC ..... A61F 2/82–945; A61B 17/12–2017/12018
See application file for complete search history.

(56) References Cited

U.S. PATENT DOCUMENTS

| | | | |
|---|---|---|---|
| 7,544,198 B2 | 6/2009 | Parodi | |
| 7,862,499 B2 | 1/2011 | Miller et al. | |
| 8,940,043 B2 | 1/2015 | Chalekian et al. | |
| 10,426,593 B2 | 10/2019 | Lick et al. | |
| 2003/0100943 A1* | 5/2003 | Bolduc | A61B 17/10 623/1.11 |
| 2003/0135269 A1 | 7/2003 | Swanstrom | |
| 2004/0096090 A1 | 5/2004 | Bascle et al. | |
| 2006/0106406 A1* | 5/2006 | Weinberger | A61B 17/1322 606/153 |
| 2008/0215134 A1* | 9/2008 | Lawrence-Brown | A61L 31/18 623/1.34 |
| 2009/0270965 A1 | 10/2009 | Sinha et al. | |
| 2010/0087907 A1* | 4/2010 | Lattouf | A61F 2/95 623/1.11 |
| 2011/0288625 A1* | 11/2011 | Morgan | A61B 17/12022 623/1.11 |
| 2013/0297009 A1* | 11/2013 | Chalekian | A61F 2/2481 623/2.1 |

FOREIGN PATENT DOCUMENTS

| | | |
|---|---|---|
| WO | 2004096090 A1 | 11/2004 |
| WO | 2004105620 A1 | 12/2004 |
| WO | 2005070307 A2 | 8/2005 |
| WO | 2009078010 A1 | 6/2009 |

\* cited by examiner

AORTIC LANDING BAND SUPPORT METHOD AND SYSTEM

CROSS-REFERENCE TO RELATED APPLICATION

This application is a continuation of U.S. application Ser. No. 17/354,629, filed Jun. 22, 2021, and issued as U.S. Pat. No. 11,617,641 on Apr. 4, 2023, the disclosure of which is hereby incorporated in its entirety by reference herein.

TECHNICAL FIELD

The present disclosure relates to building aortic landing band support methods and systems.

BACKGROUND

The use of endovascular procedures has been established as a minimally invasive technique to deliver a variety of clinical treatments in a patient's vasculature. A stent graft is an implantable device made of a tube-shaped surgical graft covering and an expanding or self-expanding frame. The stent graft is placed inside a blood vessel to bridge, for example, an aneurismal, dissected, or other diseased or torn segment of the blood vessel, and, thereby, exclude the hemodynamic pressures of blood flow from the diseased segment of the blood vessel.

Depending on the region of the aorta involved, the aneurysm may extend into areas having vessel bifurcations or segments of the aorta from which smaller "branch" arteries extend. For example, thoracic aortic aneurysms can include aneurysms present in the ascending thoracic aorta, the aortic arch, and/or branch arteries that emanate therefrom, such as the left subclavian, left common carotid, or the brachiocephalic arteries. In some cases, a branched stent graft can be used to treat such aneurysms. For example, a branched stent graft can be deployed in the main vessel (e.g., aortic arch) with a coupling extending therefrom and toward or into the branched artery (e.g., left subclavian), and a supplemental, secondary stent graft can be deployed in the branched artery and connected to the coupling.

SUMMARY

According to an embodiment, a method of providing support in an aortic region is disclosed. The method includes wrapping a landing band around an outside of a portion of an aortic vessel in a vicinity of a sinotubular junction (STJ) to form a wrapped portion of the aortic vessel. The method further includes securing the landing band to form a secured landing band. The method also includes endovascularly delivering a stent graft in a radially constricted configuration into the aortic vessel. The method also includes deploying the stent graft to a radially expanded configuration such that the stent graft contacts the wrapped portion of the aortic vessel. The method also includes connecting the stent graft in the radially expanded configuration to the secured landing band.

According to another embodiment, a method of providing support in an aortic region is disclosed. The method includes wrapping a landing band around an outside of a portion of an aortic vessel to form a wrapped portion of the aortic vessel. The landing band includes a proximal end and a distal end. The method further includes securing the landing band to itself with fasteners to form a secured landing band. The secured landing band has a landing band conical profile.

According to yet another embodiment, an aortic region support system includes a landing band configured to wrap around an outside of a portion of an aortic vessel and to secure to itself with fasteners to form a secured landing band. The landing band has a proximal end and a distal end. The secured landing band has a landing band conical profile.

BRIEF DESCRIPTION OF THE DRAWINGS

FIGS. 2-9 illustrate various steps of a method of building a landing zone for supporting a transcatheter aortic valve replacement (TAVR) device or thoracic endovascular aortic repair (TEVAR) device, such as a stent graft, in which:

FIG. 2 shows a landing band wrapped about the vessel adjacent to the STJ;

FIG. 3 shows the landing band being cinched to a desired diameter and clamped;

FIG. 4 shows the landing band being secured in its diameter with fasteners;

FIG. 5 shows a stent graft delivery system delivering a stent graft into the vessel;

FIG. 6 shows the stent graft in a radially-expanded configuration;

FIG. 7 shows the stent graft being attached to the landing band from the inside of the vessel via endoanchors;

FIG. 9 shows the completed attachment of the stent graft and the landing band.

DETAILED DESCRIPTION

Figure 1:
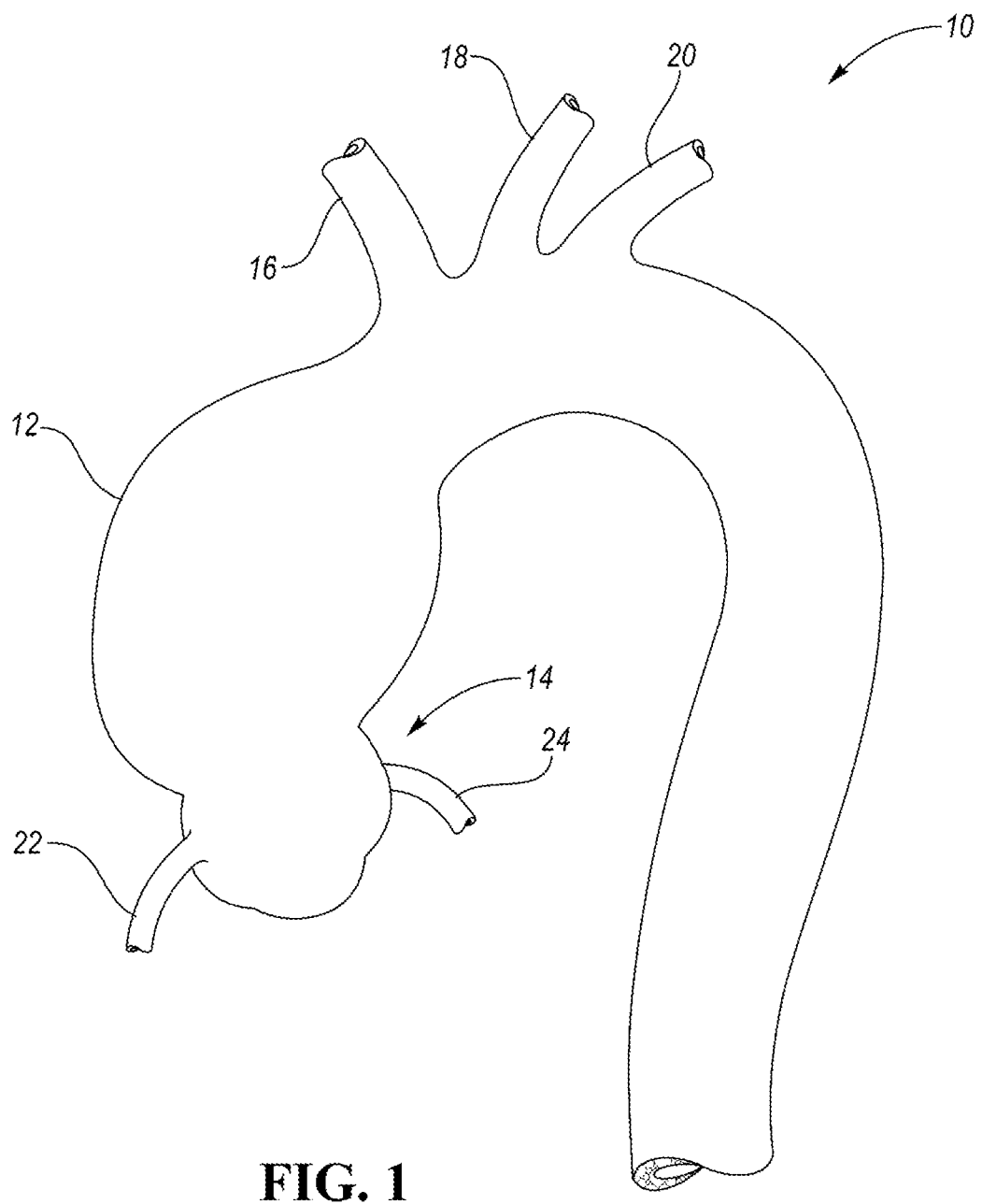
FIG. 1 is a schematic representation of an ascending aorta with an aneurism located adjacent the sinotubular junction (STJ), according to an embodiment.

Embodiments of the present disclosure are described herein. It is to be understood, however, that the disclosed embodiments are merely examples and other embodiments can take various and alternative forms. The figures are not necessarily to scale; some features could be exaggerated or minimized to show details of particular components. Therefore, specific structural and functional details disclosed herein are not to be interpreted as limiting, but merely as a representative basis for teaching one skilled in the art to variously employ the embodiments. As those of ordinary skill in the art will understand, various features illustrated and described with reference to any one of the figures can be combined with features illustrated in one or more other figures to produce embodiments that are not explicitly illustrated or described. The combinations of features illustrated provide representative embodiments for typical applications. Various combinations and modifications of the features consistent with the teachings of this disclosure, however, could be desired for particular applications or implementations.

Directional terms used herein are made with reference to the views and orientations shown in the exemplary figures. A central axis is shown in the figures and described below. Terms such as "outer" and "inner" are relative to the central axis. For example, an "outer" surface means that the surfaces faces away from the central axis, or is outboard of another "inner" surface. Terms such as "radial," "diameter," "circumference," etc. also are relative to the central axis. The terms "front," "rear," "upper" and "lower" designate directions in the drawings to which reference is made.

Unless otherwise indicated, for the delivery system the terms "distal" and "proximal" are used in the following description with respect to a position or direction relative to a treating clinician. "Distal" and "distally" are positions distant from or in a direction away from the clinician, and "proximal" and "proximally" are positions near or in a direction toward the clinician. For the stent-graft prosthesis, "proximal" is the portion nearer the heart by way of blood flow path while "distal" is the portion of the stent-graft further from the heart by way of blood flow path.

The following detailed description is merely exemplary in nature and is not intended to limit the invention or the application and uses of the invention. Although the description is in the context of treatment of blood vessels such as the aorta, the invention may also be used in any other arteries or body passageways where it is deemed useful.

Aortic anatomy is oftentimes unfavorable for sealing stent grafts during endovascular procedures in the ascending aorta. Many ascending arch aneurysms lack a proximal seal zone that is sufficient to properly seal a stent graft. FIG. 1 shows an example of ascending aorta 10 having an aneurism 12 located adjacent the sinotubular junction (STJ) 14. For context, the aorta 10 is shown with the brachiocephalic artery 16, the left common carotid artery 18, and the left subclavian artery 20, and the STJ 14 is located adjacent and distal the right coronary artery 22 and the left coronary artery 24. In some disease states, such as retrograde type A aortic dissections (RTADs) with primary entry tears or disease occurring close (e.g., within 2 centimeters) of the STJ 14, there is inadequate tissue along the aorta 10 at the STJ 14 for sealing a deployed stent graft. In short, aneurysms can sometimes be in locations that yield little amounts of healthy tissue to properly mount a stent graft. When stenting in the vicinity of the STJ 14, there is concern that the continued outward radial force from the stent graft will impact the architecture of the valve, potentially resulting in aortic insufficiency. Unfavorable anatomy limits the percent of potential patients that can be treated using a purely endovascular procedure. Currently proposed valves may not be able to seal well in cases where a calcified anulus is not present in this region. The currently proposed valves may also be prone to migration. A landing zone or band as disclosed herein in one or more embodiments may address one or more drawbacks of currently proposed valves. A landing zone or band in one or more embodiments may adequately secure stent grafts and may prevent disease progression.

Therefore, according to various embodiments described herein, a landing zone or landing band for supporting a stent graft is disclosed. Also disclosed are hybrid surgical/endovascular methods to surgically implant and install an engineered landing zone to provide a suitable seal and fixation for transcatheter aortic valve replacement (TAVR) and thoracic endovascular aortic repair (TEVAR) devices such as stent grafts and the like. To treat ascending aortic pathologies that lack an adequate natural landing zone, the landing band can be installed to provide one. The method in one or more embodiments is "hybrid" in that it involves direct access (e.g., sternotomy or partial sternotomy) to the site for installation of the landing band, as well as endovascular installation of a TAVR or TEVAR device (e.g., stent graft) once the landing band is installed. The hybrid approach in one or more embodiments may have the advantage of avoiding placing a patient on circulatory arrest or on one or more bypass pumps sometimes needed for open surgical repair. The circulatory arrest and bypass pump procedures are often associated with significant morbidity and mortality. Elderly patients with significant comorbidities may be too frail for open repairs. Other nonsurgical patients may lack good anatomy for endovascular repair. The hybrid approach in one or more embodiments may offer an alternative for some elderly patients and/or nonsurgical patients.

Figure 2:
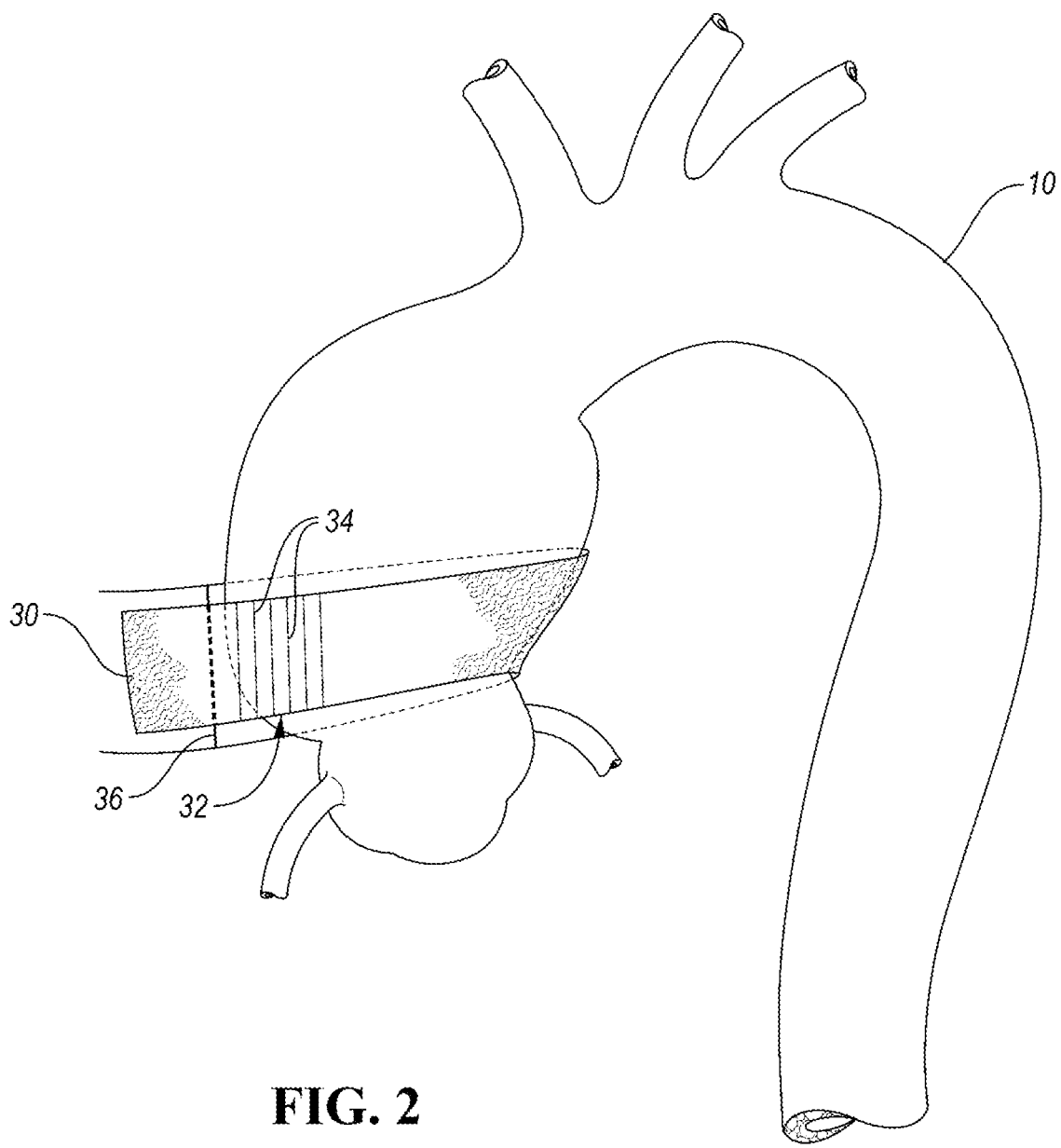

FIGS. 2-9 show sequential operations to install a landing band for providing a landing zone for fixation of a TAVR or TEVAR device, according to an embodiment. FIG. 2 illustrates an example embodiment of such a landing band 30 being installed. Once the aorta 10 has been dissected free, the landing band 30 can be fed under the aorta 10 and wrapped circumferentially around the aorta 10 to create a stable landing zone for the endograft. The landing band 30 can be made of surgical felt, polyethylene terephthalate (PET), expanded polytetrafluoroethylene (ePTFE), polyurethane (PU), or other suitable materials. In other embodiments, the landing band 30 can be made of a tissue patch (e.g., cadaver), a cellular matrix, collagen, and/or can be 3-D printed. The landing band 30 can be constructed from a thermoset shape memory polymer shape biased to a curved configuration to ease the wrapping procedure. The material of the landing band 30 can be a solid material that is woven or knitted, or can be a mesh with openings. The material of the landing band 30 can be constructed form an elastomeric material to provide a degree of compliance to the engineered landing zone and to accommodate the pulse wave of blood flow.

The landing band 30 can have a length and width (e.g., from the perspective as if the landing band 30 were stretched out and laying flat). The width of the landing band can vary, but in embodiments the width should be wide enough to provide a suitable landing zone for the endovascular device later installed. The band 30 can be shape set into a desired configuration to prevent an abrupt compliance mismatch between the band 30 and the aorta 10 or other anatomical features. For instance, with respect to an aneurysmal ascending, the taper may be conical with the larger opening facing upwards to accommodate a dilated ascending aorta by creating a gradual transition. In the setting of a dilated STJ, the larger opening of a cone may face downward to prevent an abrupt mismatch at the interface with the STJ. If desired, multiple landing bands 30 can be installed or the entire length of the ascending aorta 10 can be wrapped in landing bands 30.

As shown in the embodiment in FIG. 2, the landing band 30 may include measurement markers 32. The measurement markers 32 may include a plurality of spaced-apart lines 34 with each line 34 representing a unit of length. This allows the surgical technician to know how much of the landing band 30 is wrapped around the aorta 10, e.g., how much of a diameter the landing band 30 assumes. In one example, the inner surface of the landing band 30 has a mark 36 that is aligned with lines 34 that are spaced apart in millimeter gradations on the external surface of the band material to allow the physician to cinch the band to a prescribed diameter. Radiopaque markers can be added to the proximal and distal material edges so that the position of the band is visible during fluoroscopy.

Figure 3:
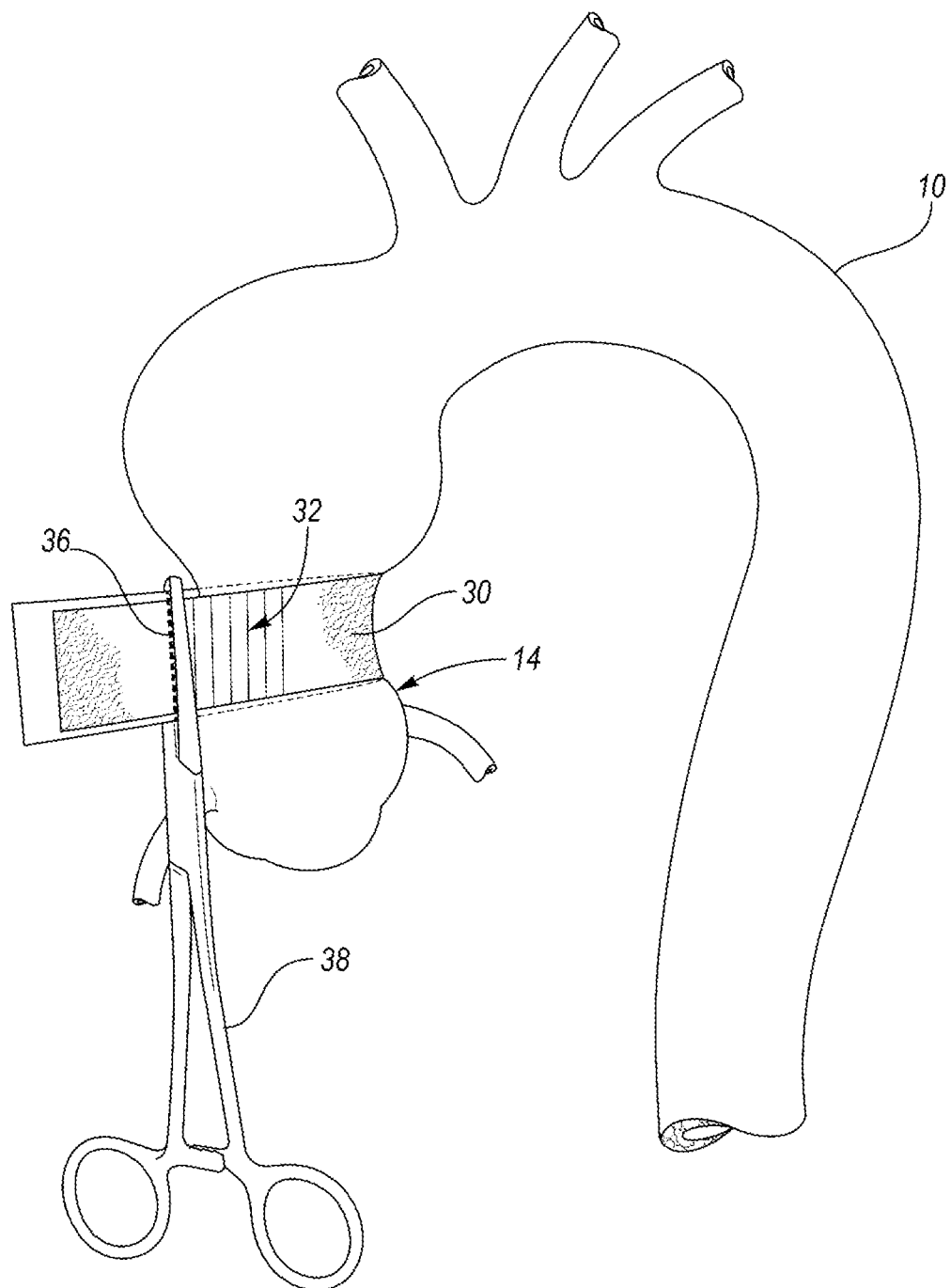

FIG. 3 shows a step after FIG. 2 in which the landing band 30 is cinched to a desired diameter using the measurement markers 32, and clamped (e.g., with hemostats 38). Alternatives to clamping may also be used, such as sutures, staples, or other mechanisms to keep the landing band 30 at the desired diameter until it can be secured. The cinch is made at a location where line 36 overlaps one of the measurement markers 32. As shown in this Figure, the band is placed and cinched at a location just distal or slightly overlapping with the STJ 14.

Figure 4:
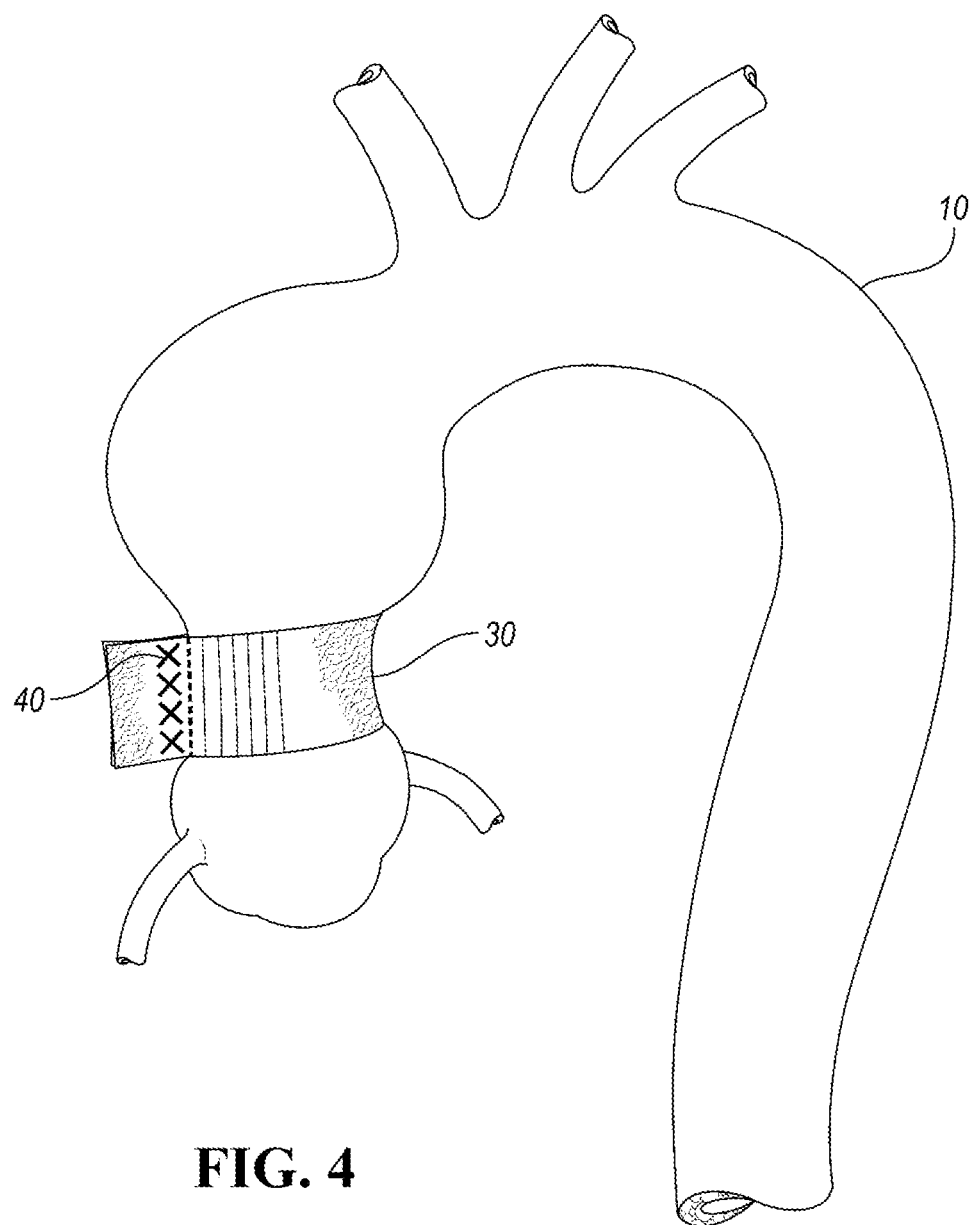

FIG. 4 shows a next step in which the landing band 30 is secured. In the illustrated embodiment, the two halves of the landing band 30 wrapping around the aorta 10 are affixed to each other by fasteners 40. The fasteners 40 may be sutures, staples, clips, or other closure mechanisms. If alternatives to clamping were used during the cinching step, those may also be the closure mechanism, or they may be removed and a new/different closure mechanism can be used to secure the landing band. Alternatively, the landing band 30 can be affixed using a hook-and-loop (e.g., VELCRO) like material or self-ratcheting mechanism. Once affixed, the loose remainder of the landing band 30 can be trimmed to the desired length.

Figure 5:
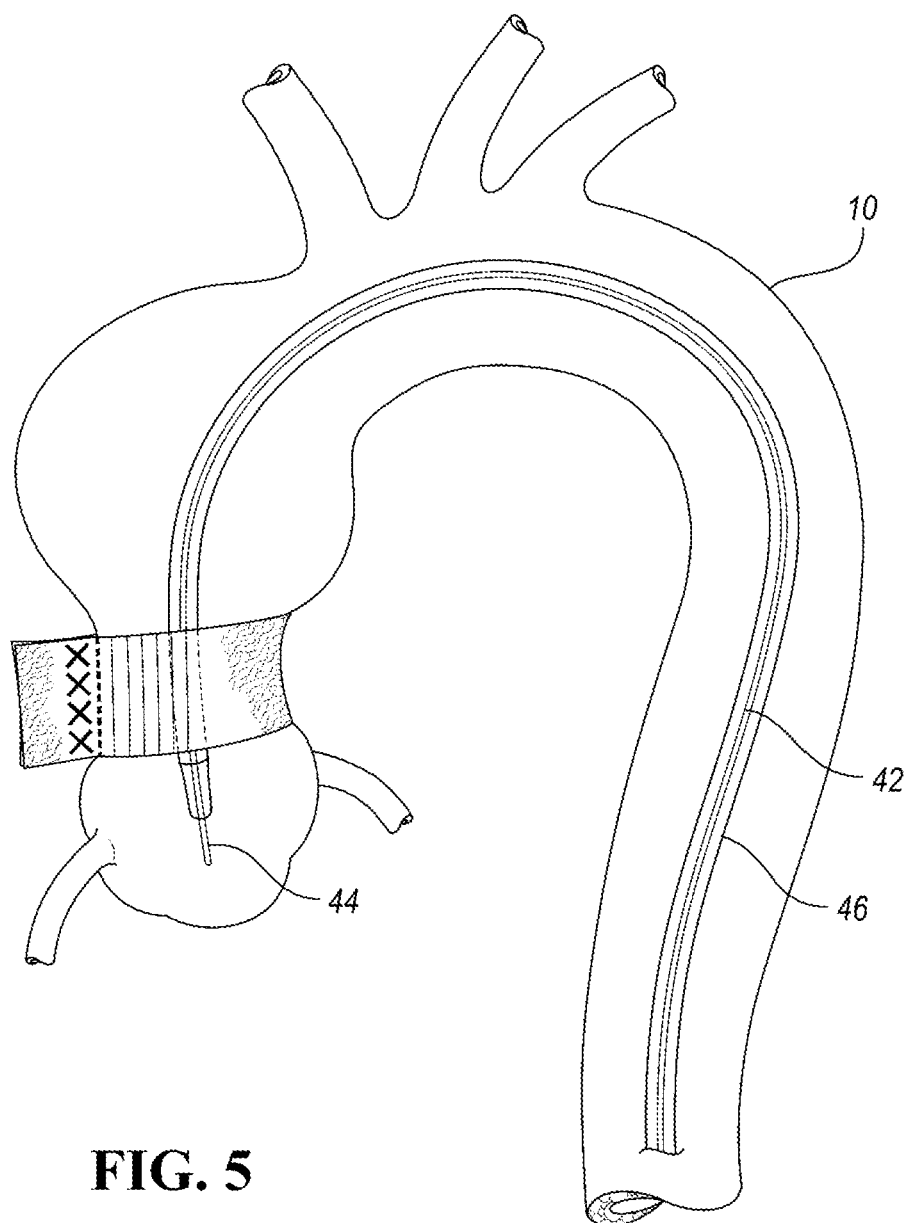

FIG. 5 shows a next step in which a stent graft 42 is delivered through the ascending aorta 10. The stent graft 42 is but one example of a TEVAR device or TAVR device that can be delivered for fixing to the landing band 30. During this step, a guidewire 44 may be fed endovascularly to the desired location in the ascending aorta 10. A stent graft delivery system such as the known VALIANT NAVION or VALIANT CAPTIVIA system sold by MEDTRONIC can track the stent graft 42 along the guidewire, with an outer sheath or lumen 46 containing the stent graft 42 therein in a radially-constricted configuration. Then, when in position, the delivery system can cause an outer lumen 46 or sheath to retract, causing the stent graft 42 to expand radially outwardly. However, the landing band 30 and the associated method(s) may be used with any TEVAR or TAVR device and delivery system.

Figure 6:
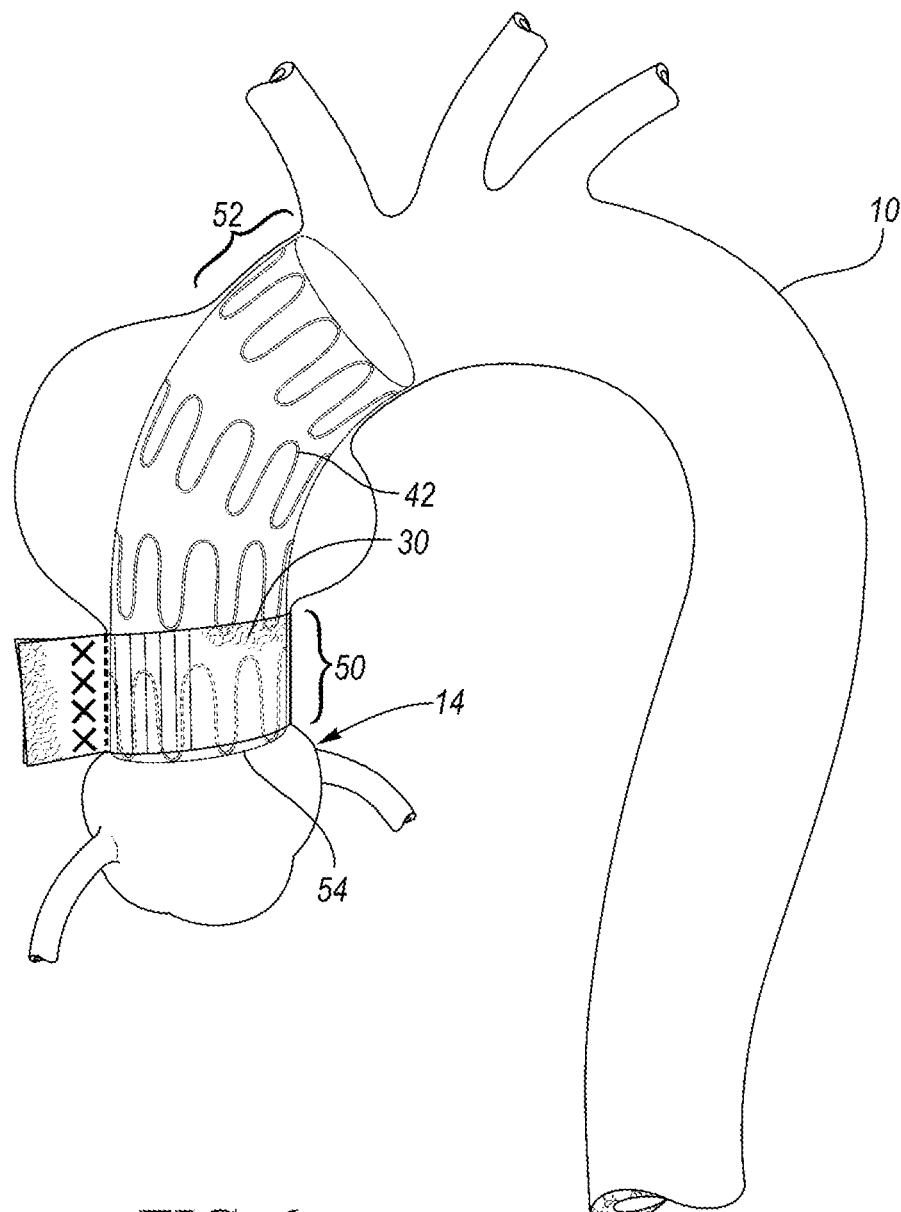

FIG. 6 shows the stent graft 42 in a fully deployed or radially-expanded configuration with the outer lumen and guidewire retracted and removed. The stent graft 42, now deployed, can achieve a seal with the landing zone created by the landing band 30 at a proximal portion 50 of the ascending aorta 10. The landing band 30 provides support of the aorta 10 and prevents the radial force of the stent graft 42 from dilating the STJ 14. The proximal portion 50 of the aorta 10 equipped with the landing band 30 can therefore be referred to as a proximal landing zone.

FIG. 6 also illustrates a distal portion 52 of the ascending aorta 10. A landing band can be placed about the distal portion 52 to create a distal landing zone. Depending upon the disease being treated and the location of the aneurism, either one or both of the distal landing zone or proximal landing zone can be created by using one or more of the landing bands 30. Alternatively, a single large landing band can be provided that wraps about the descending aorta 10 from the distal portion 52 to the proximal portion 50. The single landing band may have a width that extends from the proximal portion to the distal portion or it may have a smaller width but longer length, such that it can be helically wrapped to cover the entire height.

As can be seen in FIG. 6, a proximal end 54 of the stent graft 42 may extend proximally beyond the landing band 30. This assures that a full seal is provided between the stent graft 42 and the landing band 30. However, in other embodiments, the proximal end 54 may be landed within the landing band 30.

Because of the direct access provide by the hybrid procedure, the stent graft 42 can be permanently affixed to the landing band 30. The stent graft 42 can be affixed to the landing band 30 in any suitable manner. In one embodiment, the stent graft 42 can be affixed to the landing band 30 by suturing from the outside using a needle driver and a curved suture needle, for example. The suturing is configured to reduce susceptibility of the device to the migration force of the blood flow, thereby making the device more resistant to displacement due to cardiac and/or respiratory induced motion in the aorta. The material of the landing band 30 provides support to the aorta and prevents continued dilation of the aorta 10 due to continued disease progression. Pressure of the stent graft 42 against the landing band 30 helps prevent Type I endoleaks from forming. And, any leaks that do develop can be directly ligated because of the hybrid access.

Figure 7:
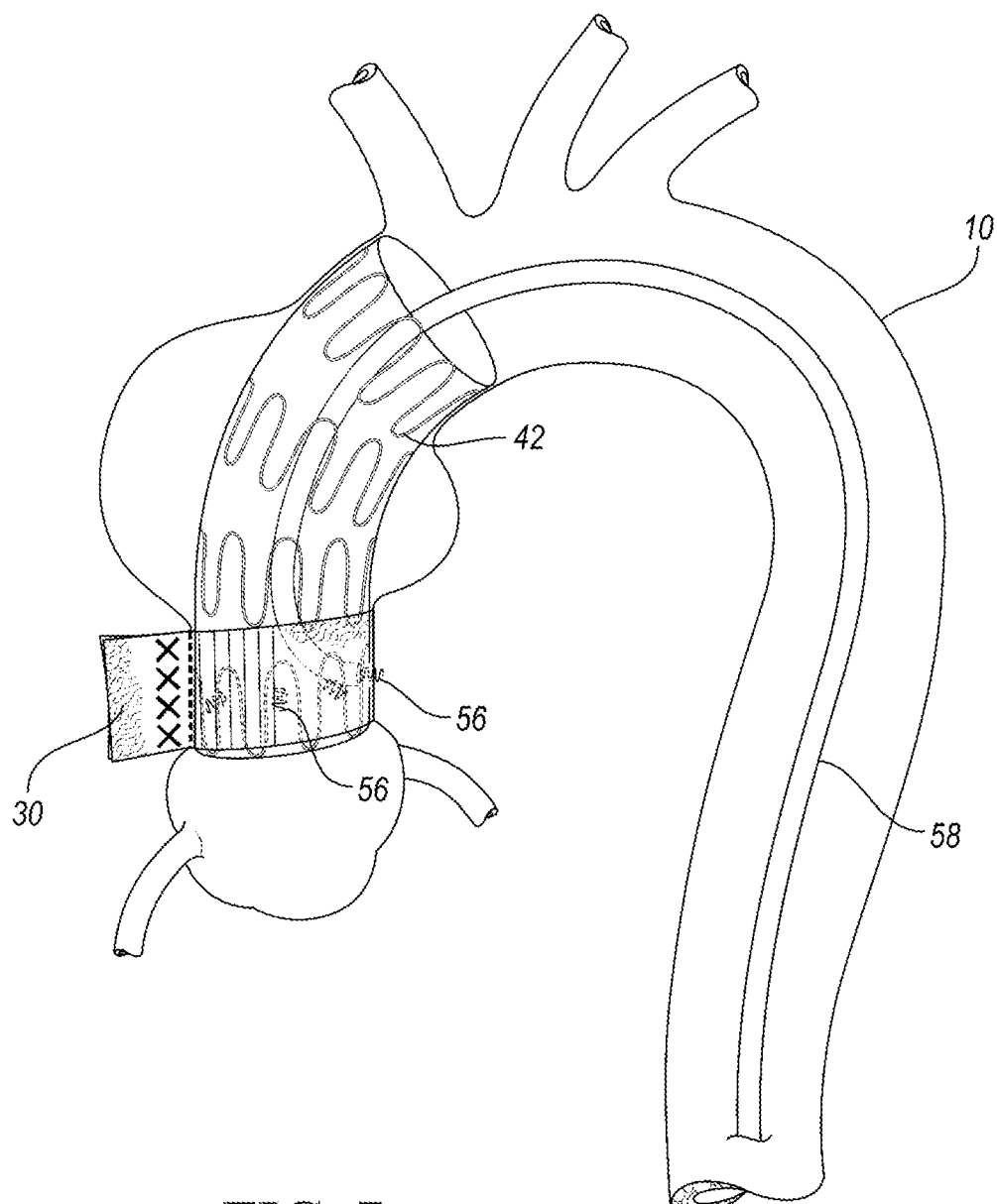

Alternatively, as illustrated in FIG. 7, the stent graft 42 can be attached to the landing band 30 from the inside of the aorta 10. This can be done endovascularly via endoanchors 56 for example. The endoanchors 56 can be deployed to target thicker segments of the landing band 30, or additional material can be added to create a robust attachment. A suitable system such as the HELI-FX ENDOANCHOR System (available from MEDTRONIC) can be utilized to deliver the endoanchors. This may include delivering an endoanchor guide 58, such as a HELI-FX guide endovascularly through the aorta 10, through the stent graft 42 and to a location of the interior of the stent graft 42 that aligns with the landing band 30. Additional description of anchoring the stent graft 42 via the endoanchors 56 is shown and described with reference to FIGS. 8A and 8B. The endoanchors 56 may be sutures, but in other embodiments the endoanchors 56 are staples, anchors, shape-memory anchors, or other fasteners.

The anchoring of the stent graft 42 to the landing band 30 is performed in the proximal portion 50 of the ascending aorta 10, but similar techniques can be used in the distal portion 52 of the ascending aorta 10 if a landing band is placed there.

Figure 8A:
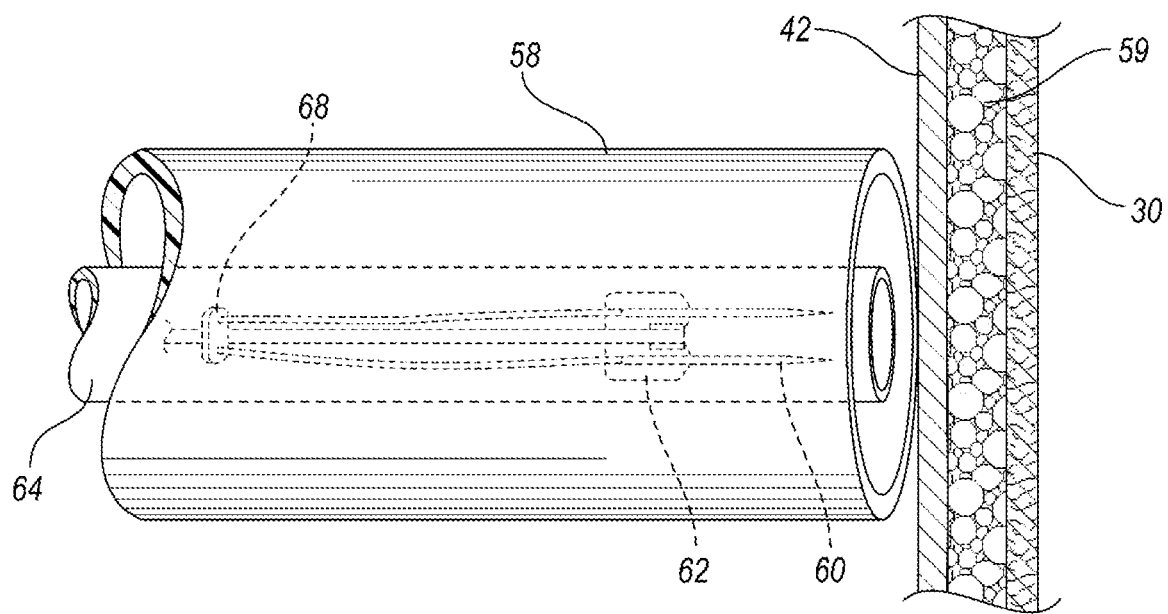
FIG. 8A shows an enlarged view of the endoanchors being delivered to the desired location within the vessel.
Figure 8B:
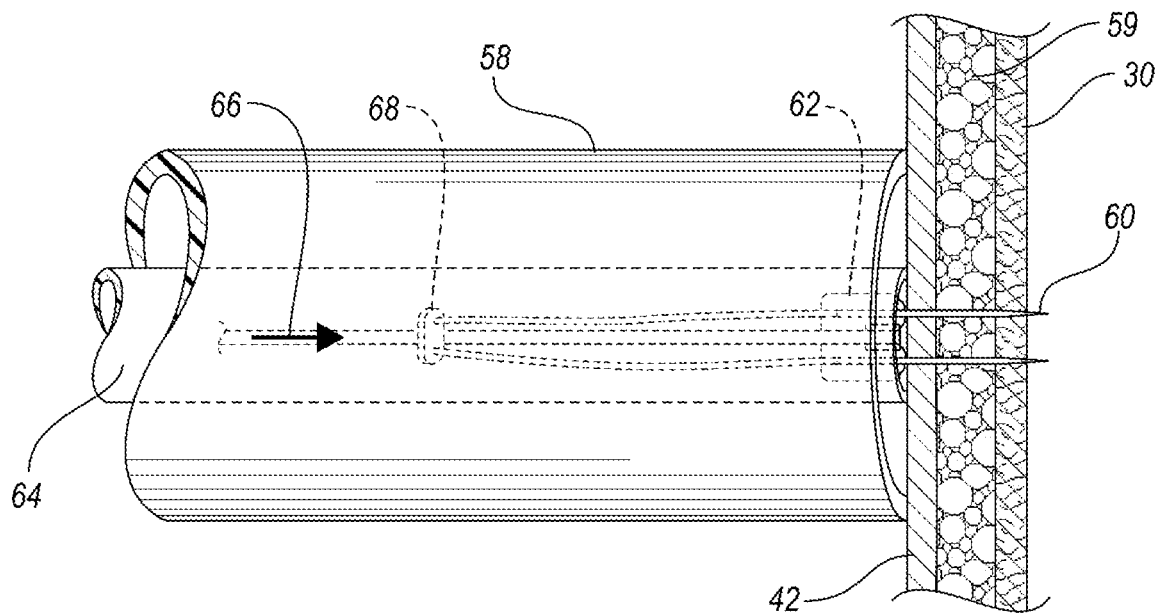
FIG. 8B shows needles carrying a suture piercing the vessel wall, the stent graft, and the landing band to allow tying of the suture from the outside of the vessel.
Figure 9:
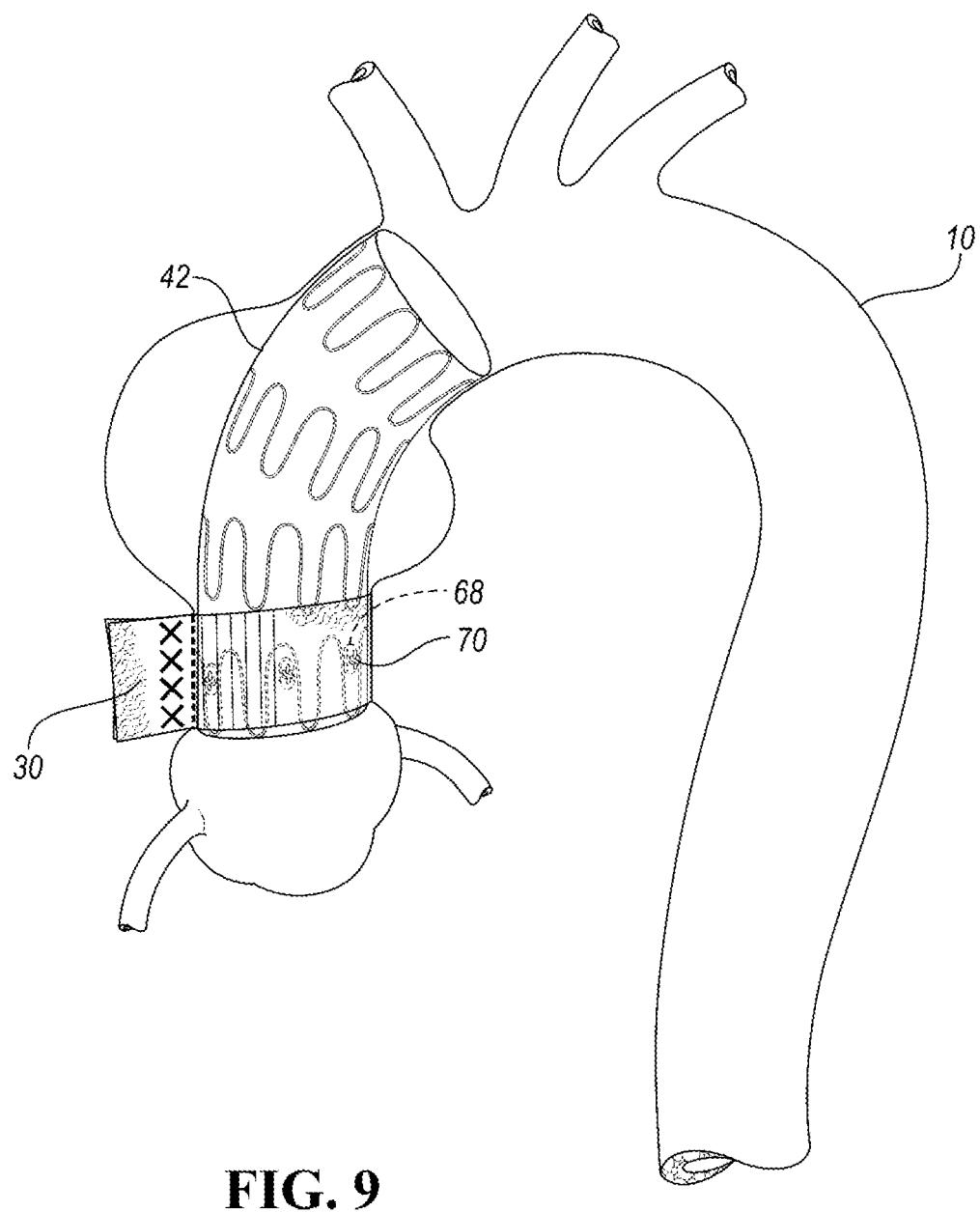

Referring to FIG. 8A, the end of the endoanchor guide 58 is shown engaging the portion of the aorta 10 (e.g., a vessel wall 59) that is wrapped with the landing band 30 as shown in FIG. 7. Once the endoanchor guide 58 is delivered to the site (e.g., endovascularly), the endoanchors 56 can be deployed. According to the illustrated embodiment, a pair of needles 60 engaged within a needle holder 62 within a protective sheath 64 or lumen can be tracked through the endoanchor guide 58 and positioned perpendicular to the vessel wall 59. The size of the needles 60 and the space therebetween can be determined by the size and spacing of the needle holder 62. Then, the needle holder 62 is advanced so that the needles 60 are pushed through the graft material of the stent graft 42, through the vessel wall 59, and through the landing band 30. This is shown in FIG. 8B, and the advancement is shown by arrow 66. The needles 60 can then be grasped from the outside of the vessel wall 59 by the surgical technician, and sutures 70 (as shown in FIG. 9) can be pulled taut until a pledget 68 contacts stent graft 42 positioned on the inside of the vessel wall 59. Surgical knots can be used to tie the sutures 70 from the outside of the vessel wall 59. The needles 60 along with excess amount of suture can be cut and removed thereafter. Additional pledgets can be added to the outside of the vessel wall 59 prior to tying the surgical knots. This procedure can be repeated depending on the implementation to adequately secure the landing band 30 to the vessel wall 59 of the aorta 10.

FIG. 9 shows the aorta 10 with the landing band 30 attached thereto via the sutures 70 as described with reference to FIGS. 8A-8B. Pledgets 68 are shown within the interior of the landing band 70, with each pledget 68 contacting the stent graft positioned on the inside of the vessel wall of the aorta 10 from the suturing steps described herein.

Figure 10:
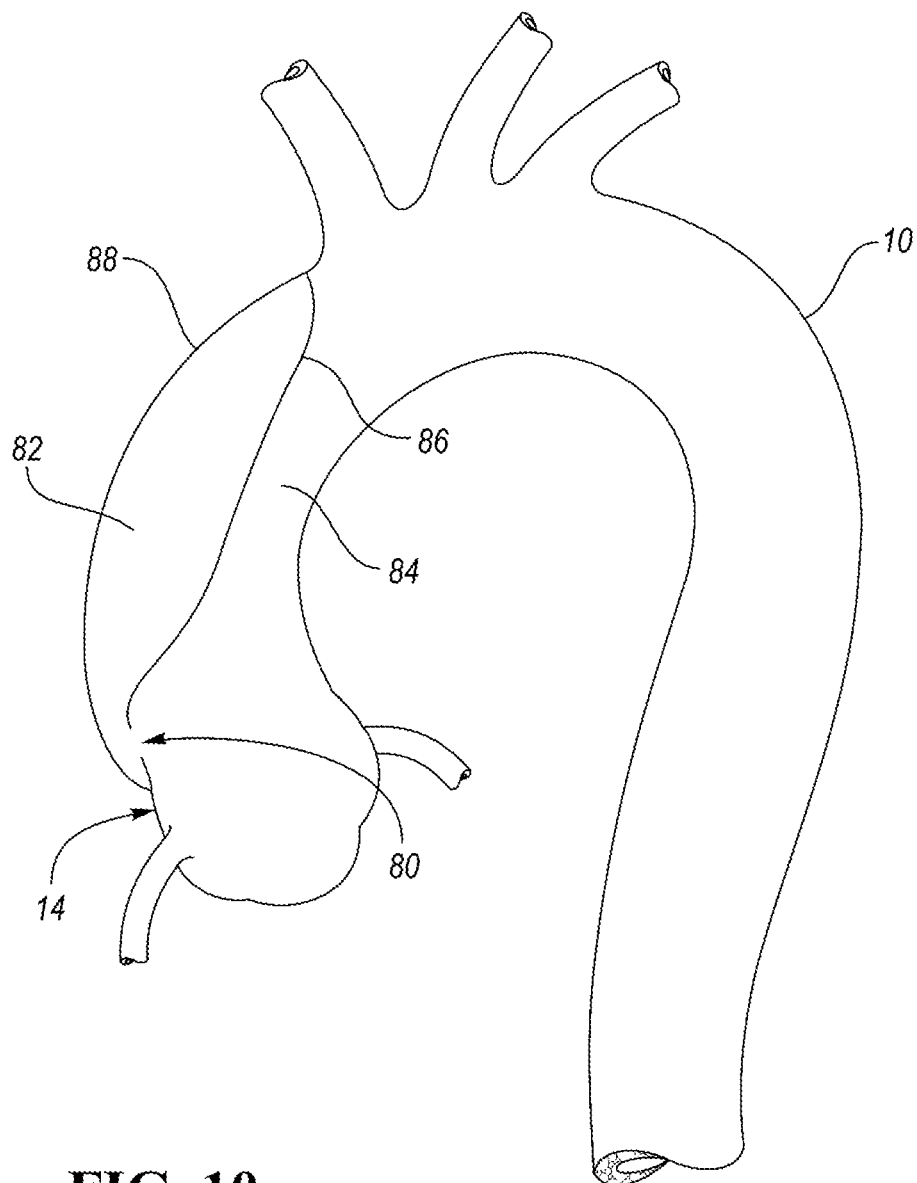
FIG. 10 shows a vessel with a retrograde type A aortic dissection (RTAD).
Figure 11:
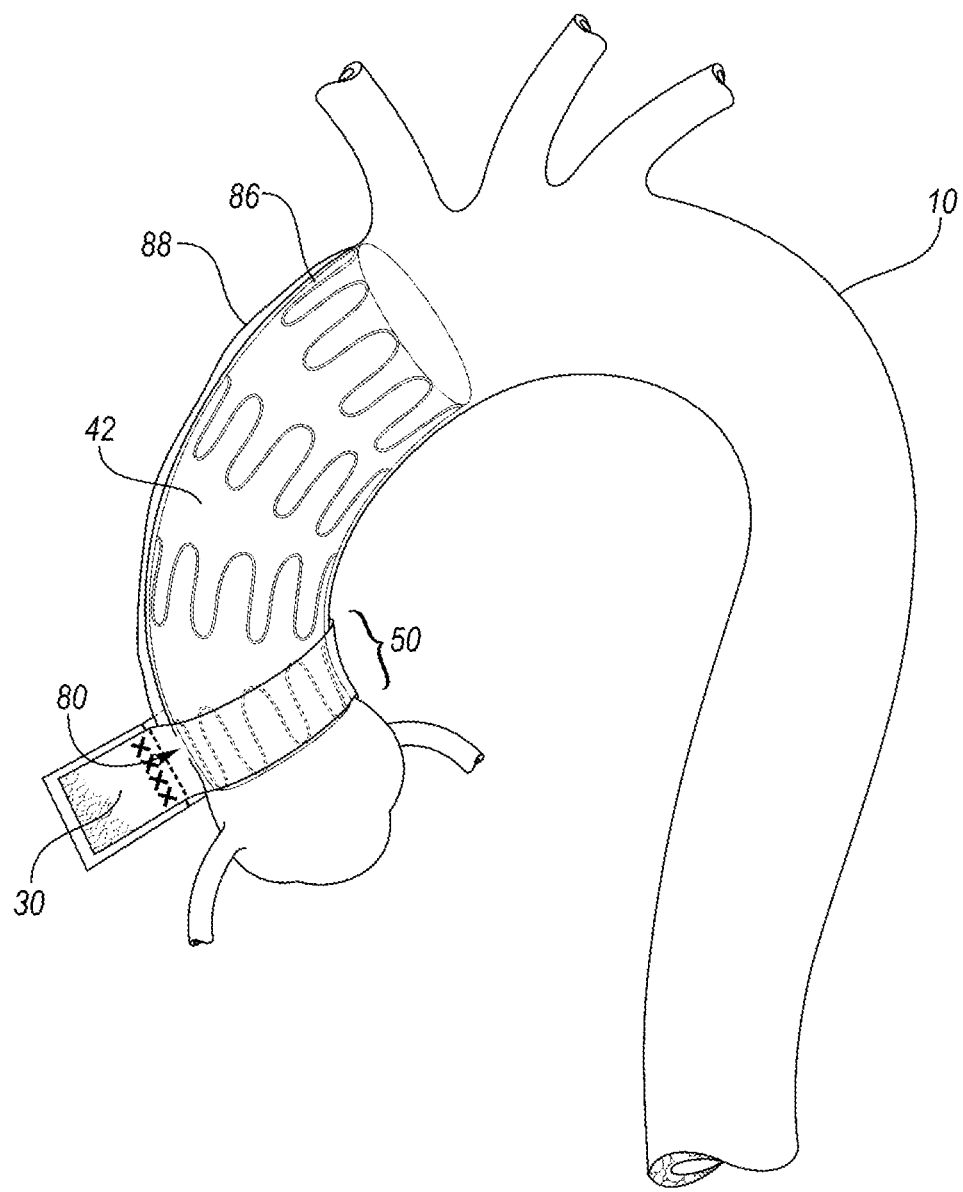
FIG. 11 shows the vessel of FIG. 10 with a landing band secured in a location that overlaps the primary entry tear and adjacent the STJ.

FIGS. 10-11 illustrate a similar procedure used to create a suitable landing zone in cases of retrograde type A aortic dissection (RTAD) within the aorta 10. FIG. 10 shows an RTAD with a primary entry tear 80 existing near the STJ 14. The primary entry tear 80 is a tear in the aorta wall that creates a false lumen 82 separated from a true lumen 84 of the aorta 10. A dissection septum 86 is a weak, thin membrane that separates the false lumen 82 from the true lumen 84. If left untreated, this can potentially be fatal. So, the landing band 30 can be used to compress the outer wall 88 of the aorta 10, allowing the thinner, weakened septum 86 to be reinforced and heal.

As shown in FIG. 11, once again a proximal seal zone can be created by attaching a landing band 30 at the location of the primary entry tear 80, at a proximal portion 50 of the ascending aorta 10 adjacent the STJ 14. The landing band 30 and stent graft 42 can be attached and deployed as described previously. Due to the landing band 30, the primary entry tear 80 and dissection septum 86 are pushed up against the landing band 30 by the self-expanding endovascular sent graft 42, preventing flow into the primary entry tear 80. A traditional stent graft would not be able to seal at the proximal portion 50 due to the location of the primary entry tear 80 and the lack of a proximal seal zone for the stent graft; the landing band 30 placed at this location is optimal to treat this disease. The stent graft 42 can be permanently affixed to the landing band 30 as described above.

Figure 12:
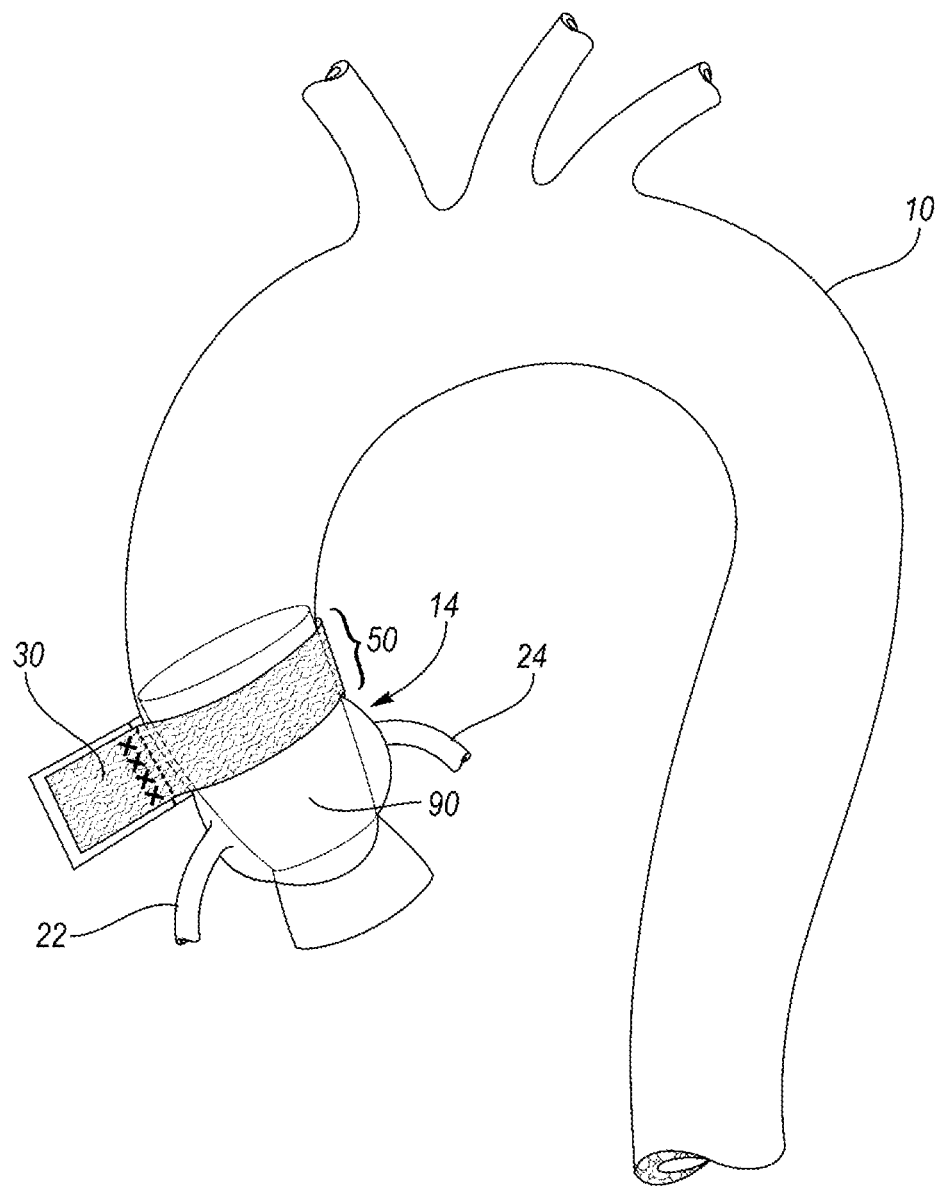
FIG. 12 shows an embodiment in which the landing band is used to support a valve delivered endovascularly.

FIG. 12 shows an embodiment of utilizing a landing band in a TAVR procedure. In cases of aortic insufficiency when suitable securement of the aortic valve is not possible, the landing band 30 can be established using the hybrid approach described herein. The landing band 30 is again placed at a proximal portion 50 of the aorta 10. A valve 90 with a long superstructure is deployed using known TAVR procedures. The valve 90 may extend proximally beyond the right coronary artery 22 and the left coronary artery 24. The right coronary artery 22 and the left coronary artery 24 are perfused through the open cell design of the frame of the valve 90. The superstructure of the valve frame can be permanently affixed to the landing band 30 to prevent dislodgment or movement of the valve 90 utilizing the teachings described above. The landing band 30 can provide support for the aorta 10 at the STJ 14 to prevent dilation due to the radial force of the valve 90. This may improve valve function in the setting of aortic insufficiency. This may also help prevent reoccurrence of AI due to the continued dilation of a diseased aortic root and/or proximal ascending aorta.

The valve 90 is shown as cone-shaped, but other shapes can be utilized to conform to the anatomy. Also, cinching of the landing band 30 may be performed to assume a smaller diameter for the TAVR procedure than as described in the above embodiments.

Figure 13:
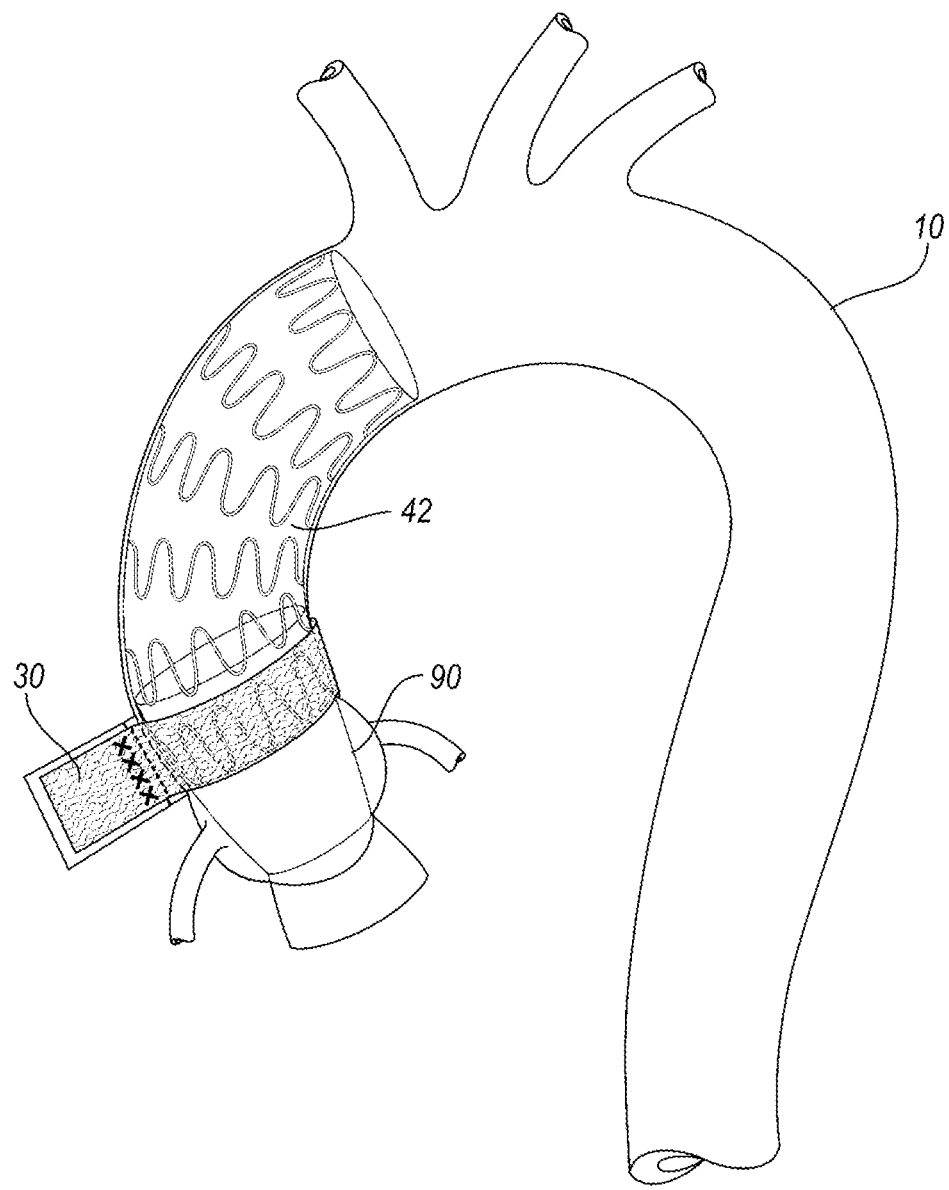
FIG. 13 shows an embodiment in which a stent graft is deployed and is also supported by the same landing band that supports the valve.

Since there is not an abundance of space in the area of the natural ascending aorta 10 for securement of grafts, valves, and the like, the landing band 30 gives additional structure for adequate mounting and securement. FIG. 13 shows an embodiment in which a stent graft 42 is also secured to the landing band 30. In this embodiment, the valve 90 and stent graft 42 are both attached to the landing band 30. A single suture can pass through both the stent graft 42 and the valve 90, as well as the vessel wall and the landing band 30, using the methods described in one or more of the embodiments set forth herein. One or more embodiments may be applicable in the setting of a valve being placed into anatomy with a dilated STJ and/or a diseased ascending aorta. In this scenario, there is no proximal seal for the stent graft and perfusion of the coronary arteries through the superstructure of the valve frame may continue to perfuse the ascending pathology. There is not an effective proximal seal zone for the stent graft and coronary perfusion may result in a large type I endoleak. In addition to stabilization of the valve, the band of one or more embodiments may allow continued perfusion of the coronary arteries while building in a landing zone for a stent graft to exclude one or more distal pathologies.

While embodiments are described herein with respect to a stent graft having no branches (e.g., cylindrical or tubular stent grafts), aspects of these embodiments may also be used in branched stent grafts, such as that disclosed in U.S. patent application Ser. No. 17/066,035 which is hereby incorporated by reference in its entirety. The teachings described herein are not intended to be limited to only the stent graft disclosed and illustrated herein, nor to only the particular location of the aorta shown in the Figures. Rather, the teachings provided herein can be implemented using several other types of stent grafts and can be employed at several other locations within the human anatomy where inadequate artery tissue is provided for landing and sealing a stent graft.

While exemplary embodiments are described above, it is not intended that these embodiments describe all possible forms encompassed by the claims. The words used in the specification are words of description rather than limitation, and it is understood that various changes can be made without departing from the spirit and scope of the disclosure. As previously described, the features of various embodiments can be combined to form further embodiments of the invention that may not be explicitly described or illustrated. While various embodiments could have been described as providing advantages or being preferred over other embodiments or prior art implementations with respect to one or more desired characteristics, those of ordinary skill in the art recognize that one or more features or characteristics can be compromised to achieve desired overall system attributes, which depend on the specific application and implementation. These attributes can include, but are not limited to cost, strength, durability, life cycle cost, marketability, appearance, packaging, size, serviceability, weight, manufacturability, ease of assembly, etc. As such, to the extent any embodiments are described as less desirable than other embodiments or prior art implementations with respect to one or more characteristics, these embodiments are not outside the scope of the disclosure and can be desirable for particular applications.

What is claimed is:
1. An aortic vessel support system comprising:
   a landing band configured to wrap around a portion of an aortic vessel and having proximal and distal portions spaced apart from the portion of the aortic vessel, the proximal and distal portions of the landing band secured with fasteners at a secured portion spaced apart from the portion of the aortic vessel and having a landing band conical profile; and a valve configured to be delivered endovascularly to the portion of the aortic vessel.

2. The aortic vessel support system of claim 1, wherein the valve has a cone shape.

3. The aortic vessel support system of claim 1, further comprising:
a stent graft configured to be delivered endovascularly to the portion of the aortic vessel.

4. A method of providing support in an aortic region, the method comprising:
wrapping a landing band around an outside of a portion of an aortic vessel to form a wrapped portion, the landing band having proximal and distal portions spaced apart from the wrapped portion;
securing the proximal and distal portions of the landing band with fasteners at a secured portion spaced apart from the wrapped portion to form a secured landing band;
endovascularly delivering and deploying a valve such that the valve contacts the wrapped portion; and
connecting the valve to the secured landing band.

5. The method of claim 4, wherein the landing band has a landing band conical profile.

6. The method of claim 5, wherein the valve has a valve conical profile following a contour of the landing band conical profile.

7. The method of claim 4, wherein the valve extends beyond the proximal and distal ends of the landing band.

8. The method of claim 4, further comprising:
endovascularly delivering and deploying a stent graft such that the stent graft contacts the wrapped portion; and
connecting the stent graft to the secured landing band.

9. The method of claim 4, wherein the proximal and distal portions extend away from the wrapped portion.

10. A method of providing support in an aortic region, the method comprising:
wrapping a landing band around an outside of a portion of an aortic vessel in a vicinity of a sinotubular junction (STJ) to form a wrapped portion, the landing band having proximal and distal portions spaced apart from the wrapped portion, the landing band having a landing band conical profile;
securing the proximal and distal portions of the landing band with fasteners at a secured portion spaced apart from the wrapped portion to form a secured landing band;
endovascularly delivering a stent graft in a radially constricted configuration into the aortic vessel;
deploying the stent graft to a radially expanded configuration such that the stent graft contacts the wrapped portion; and
connecting the stent graft in the radially expanded configuration to the secured landing band.

11. The method of claim 10, wherein the connecting step includes endovascularly connecting the stent graft in the radially expanded configuration to the secured landing band.

12. The method of claim 11, wherein the connecting step includes endovascularly connecting the stent graft in the radially expanded configuration to the secured landing band via anchors.

13. The method of claim 12, wherein the anchors are endoanchors.

14. The method of claim 12, wherein the anchors are sutures, staples, and/or fasteners.

15. The method of claim 12, wherein the anchors are shape-memory anchors.

16. The method of claim 10, wherein the connecting step includes surgically connecting the stent graft in the radially expanded configuration to the secured landing band.

17. The method of claim 16, wherein the connecting step includes surgically connecting the stent graft in the radially expanded configuration to the secured landing band via needles.

18. The method of claim 17, wherein the connecting step includes surgically connecting the stent graft in the radially expanded configuration to the secured landing band via needles using a needle driver.

19. The method of claim 10, wherein the secured portion following a line along proximal and distal widths of the proximal and distal portions, respectively.

20. The method of claim 10, wherein the proximal and distal portions of the landing band extend away from the wrapped portion.

* * * * *